United States Patent
McGuinness et al.

(10) Patent No.: US 10,137,423 B2
(45) Date of Patent: Nov. 27, 2018

(54) DEVICES AND METHODS FOR MEASURING ANALYTE CONCENTRATION

(71) Applicant: Schlumberger Technology Corporation, Sugar Land, TX (US)

(72) Inventors: Kay McGuinness, Cambridgeshire (GB); Nathan Scott Lawrence, Cambridgeshir (GB); Andrew Meredith, Cambridge (GB); Andrew Warrillow, Cambridge (GB); Laurent Pirolli, Stafford, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 406 days.

(21) Appl. No.: 14/810,461

(22) Filed: Jul. 27, 2015

(65) Prior Publication Data
US 2016/0033446 A1    Feb. 4, 2016

Related U.S. Application Data

(60) Provisional application No. 62/030,616, filed on Jul. 30, 2014.

(51) Int. Cl.
*G01N 27/404*    (2006.01)
*B01F 11/02*    (2006.01)
*B01F 13/08*    (2006.01)
*B01F 11/00*    (2006.01)
*G01N 33/28*    (2006.01)

(52) U.S. Cl.
CPC ...... *B01F 13/0818* (2013.01); *B01F 11/0048* (2013.01); *B01F 11/0082* (2013.01); *B01F 11/0266* (2013.01); *B01F 13/089* (2013.01); *G01N 33/2823* (2013.01); *G01N 33/2841* (2013.01); *G01N 27/4045* (2013.01)

(58) Field of Classification Search
CPC ................ B01F 13/0818; B01F 13/089; B01F 11/0048; B01F 11/0082; B01F 11/0266; G01N 27/4045; G01N 27/4163; G01N 27/30; G01N 33/2823; G01N 33/2841
See application file for complete search history.

(56) References Cited

U.S. PATENT DOCUMENTS

2002/0127630 A1* 9/2002 DiGuiseppi ............ C12M 29/04
                                                                435/34
2009/0057147 A1* 3/2009 Kayyem ............... B01L 3/5027
                                                             204/403.01

OTHER PUBLICATIONS

Huh et al., Electrophoresis, 2007, 4748-4757.*
L.C. Clark, "Monitor and Control of Blood and Tissue Oxygen Tensions," Transactions of the American Society for Artificial Internal Organs, vol. 2, 1956, pp. 41-48.
V. Linek, V. Vacek, J. Snikule, V. Vacek, "Measurements of Oxygen by membrane-Covered Probes; Guidelines for Applications in Chemical and Biochemical Engineering," John Wiley & Sons, 1988.
C. E. Banks, A. S. Yashina, G. J. Tustin, V. G. H. Lafitte, T. G. J. Jones, N. S. Lawrence, "Exploring Alkylated Ferrocene Sulfonates as Electrocatalysts for Sulfide Detection," Electroanalysis, vol. 19, Issue 24, Dec. 2007, p. 2518-2522.

* cited by examiner

*Primary Examiner* — Gurpreet Kaur
(74) *Attorney, Agent, or Firm* — Sara K. M. Hinkley

(57) ABSTRACT

Disclosed herein are devices and methods for the detection, quantification and/or monitoring of analytes. The systems and methods can be used, for example, to rapidly monitor gases downhole in a well.

20 Claims, 13 Drawing Sheets

DEVICES AND METHODS FOR MEASURING ANALYTE CONCENTRATION

CROSS REFERENCE TO RELATED APPLICATIONS

This application claims the benefit of priority to U.S. Provisional Patent Application 62/030,616, filed on Jul. 30, 2014, the entire content of which is incorporated herein by reference.

TECHNICAL FIELD

The subject matter disclosed herein generally relates to devices and methods for the detection, quantification and/or monitoring of analytes. The systems and methods can be used, for example, to rapidly monitor gases downhole in a well.

BACKGROUND

To date, there are no production logging sensors capable of measuring downhole gases (such as $H_2$, $O_2$, $CO_2$, $CH_4$, $C_2H_6$, $H_2S$). However, knowledge of these species within a reservoir fluid would aid in deciding which, if any, downhole zones should be isolated; deciding on which materials should be used for pipelines and, in the case of $H_2S$, provide a means of knowing where a scavenger should be injected and how much scavenger is required.

SUMMARY

Provided herein are devices and methods for the detection, quantification and/or monitoring of analytes, including $H_2S$, in liquid samples. The systems and methods can be used, for example, to rapidly monitor gases downhole in a well.

Suitable devices can comprise a membrane that allows diffusion of an analyte. The device can include an active measuring area for measuring a concentration of the analyte and a sensing chamber situated between the membrane and the active measuring area. The sensing chamber can include a wall and can further comprise a mediating fluid.

In some examples, the device can further include an element for producing convection within the mediating fluid. The element can facilitate mixing of the analyte diffusing through the membrane in the mediating fluid to thereby reduce a response time for the active measuring area to measure the presence of the analyte in the mediating fluid.

In some examples, the element comprises a magnetic stirrer placed inside the sensing chamber. The device can further comprise an external magnetic drive positioned outside the sensing chamber for activating the magnetic stirrer.

In some examples, the element comprises a magnet tethered to a shim positioned in the mediator fluid and an electromagnet positioned outside the sensing chamber, wherein the shim is capable of vibrating when subjected to a magnetic field from the electromagnet.

In some examples, the device further comprises a diaphragm adjacent the sensing chamber and the element is capable of vibrating the diaphragm to agitate the mediator fluid. The element, for example, can comprise a motor driven agitator, a pulsed solenoid agitator, a high frequency ultrasonic agitator, or combinations thereof positioned outside the sensing chamber capable of agitating the mediator fluid through the diaphragm.

In some examples, the element comprises a high frequency ultrasonic agitator positioned inside the sensing chamber that is capable of agitating the mediator fluid. In some examples, the element comprises an electroactive polymer adjacent the mediating fluid.

Also disclosed herein are methods of measuring an analyte concentration of a testing fluid. The method can comprise providing a device. The device can comprise any of the devices described herein. In some examples, the device is provided downhole in a well.

In some examples, the method further comprises contacting a testing fluid with the membrane for a time sufficient to allow the analyte when present to diffuse through the membrane into the mediating fluid of the sensing chamber. The testing fluid can comprise, for example, a well fluid, a biogas, water, or combinations thereof. The method can further comprise producing convection in the sensing chamber using the element to facilitate mixing of the mediating fluid. In some examples, the method further comprises measuring the analyte concentration adjacent the active measuring area.

The description below sets forth details of one or more embodiments of the present disclosure. Other features, objects, and advantages will be apparent from the description, the drawing and the claims.

BRIEF DESCRIPTION OF THE DRAWINGS

The accompanying figures, which are incorporated in and constitute a part of this specification, illustrate several aspects described below.

Like reference numbers and designations in the various drawings indicate like elements.

DETAILED DESCRIPTION

The present disclosure now will be described more fully hereinafter with reference to specific exemplary embodiments. Indeed, the present disclosure can be embodied in many different forms and should not be construed as limited to the embodiments set forth herein.

Provided herein are devices and methods for the detection, quantification and/or monitoring of analytes, including $H_2S$, in liquid samples. The systems and methods can be used, for example, to rapidly monitor gases downhole in a well. Also disclosed herein are methods of measuring an analyte concentration of a testing fluid using a device as described herein.

Downhole gas chemical sensors can use a gas permeable membrane to separate the sensing environment from the harsh/fouling media commonly found within an oilfield wellbore. Such a system can either operate in a flux mode in which the gas molecules passing through the membrane are reacted with and/or detected continuously, as in the case of an electrochemical Clark cell. In such systems rapid detection can be achieved as the detector is placed just behind the membrane. However, should the properties of the membrane alter during the course of the measurement, it could have a dramatic effect on the measurement as the output is proportional to the rate of transport through the membrane. To overcome these problems, the sensor can work in an alternative mode, which is known as an equilibrium measurement. In this case the gas is allowed to diffuse through the membrane into the sample chamber until the gas concentration within the sample chamber is in equilibrium with the external flowline. This measurement therefore negates any changes in the membrane properties (due to swelling or dehydration); however, a certain amount time can be needed for the cell to reach equilibrium, which could be the rate determining step.

For production logging sensors there are operational constraints to the measurements, as the sensors will need to respond quickly (less than 10 minutes) so that the tool does not get stuck in the hole and to keep rig costs to a minimum.

Figure 1:
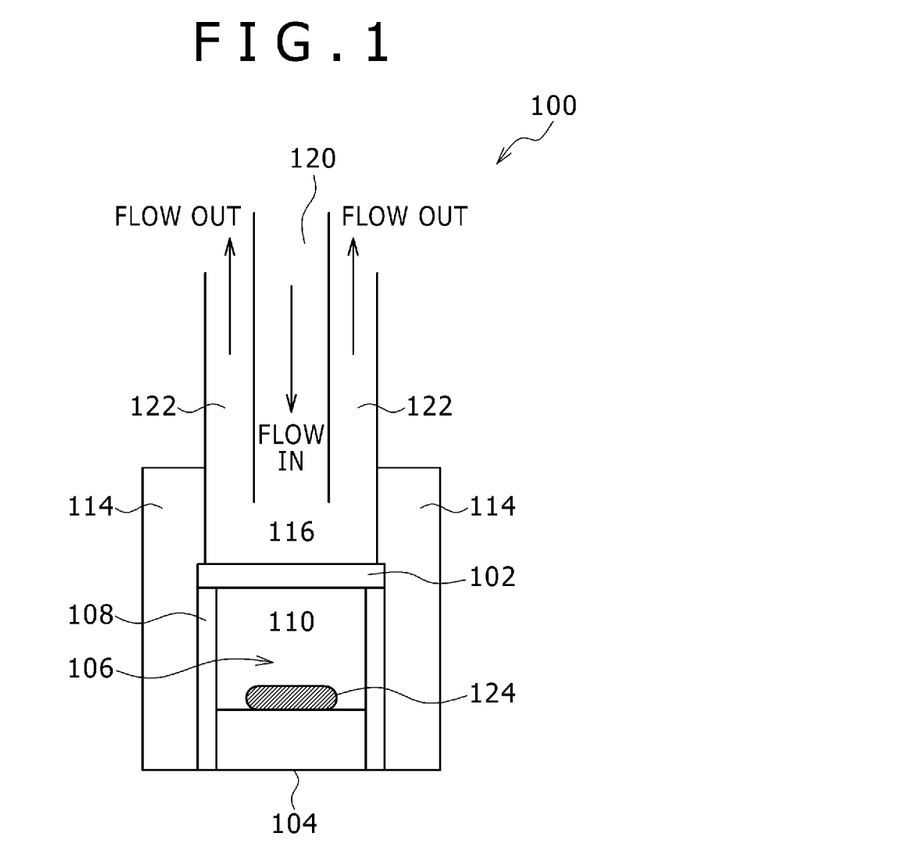
FIG. 1 displays a schematic drawing of a device according to some embodiments including a magnetic stirrer.

Referring now to FIG. 1, a device (100) according to some embodiments can include a membrane (102) that allows diffusion of an analyte. The analyte can be, for example, $H_2$, $O_2$, $CO_2$, $CH_4$, $C_2H_6$, or a combination thereof. The device (100) can further include an active measuring area for measuring a concentration of the analyte, such as an electrode (104) in the case of an electrochemical device. The device (100) can further include a sensing chamber (106) situated between the membrane (102) and the electrode (104). The sensing chamber can include a wall (108) and can further comprise a mediating fluid (110). The sensing chamber (106) can be defined by the membrane (102), the electrode (104) and the chamber wall (108). In some examples, the device (100) can further include a housing (114). The housing (114) can, for example, enclose at least a portion of the device (100). In some examples, the device (100) further comprises a first channel (120) for directing the flow of a testing fluid (116) towards the membrane (102) and at least one second channel (122) for directing the flow of the testing fluid (116) away from the membrane (102).

The distance between the membrane (102) and the active measuring area (104) can be configured to reduce the response time for measuring the presence of the analyte. In some examples, the distance between the membrane (102) and the active measuring area (104) is 0.5 mm or greater (e.g., 0.6 mm or greater, 0.7 mm or greater, 0.8 mm or greater, 0.9 mm or greater, 1.0 mm or greater, 1.1 mm or greater, 1.2 mm or greater, 1.3 mm or greater, 1.4 mm or greater, 1.5 mm or greater, 1.6 mm or greater, 1.7 mm or greater, 1.8 mm or greater, 1.9 mm or greater, 2.0 mm or greater, 2.1 mm or greater, 2.2 mm or greater, 2.3 mm or greater, or 2.4 mm or greater). In some examples, the distance between the membrane (102) and the active measuring area (104) is 2.5 mm or less (e.g., 2.4 mm or less, 2.3 mm or less, 2.2 mm or less, 2.1 mm or less, 2.0 mm or less, 1.9 mm or less, 1.8 mm or less, 1.7 mm or less, 1.6 mm or less, 1.5 mm or less, 1.4 mm or less, 1.3 mm or less, 1.2 mm or less, 1.1 mm or less, 0.9 mm or less, 0.8 mm or less, 0.7 mm or less, or 0.6 mm or less). In some examples, the distance between the membrane (102) and the active measuring area (104) is 0.5 to 2.5 mm (e.g., 0.5 to 1.1 mm).

In some examples, the device (100) can further include an element for producing convection within the mediating fluid (110). The element can facilitate mixing of the mediating fluid (110) and thus the analyte diffusing through the membrane (102) in the mediating fluid (110). This reduces the response time for the active measuring area (i.e., the electrode) (104) to measure the presence of the analyte in the mediating fluid (110). Some examples of suitable means for producing convection are disclosed herein.

Figure 2:
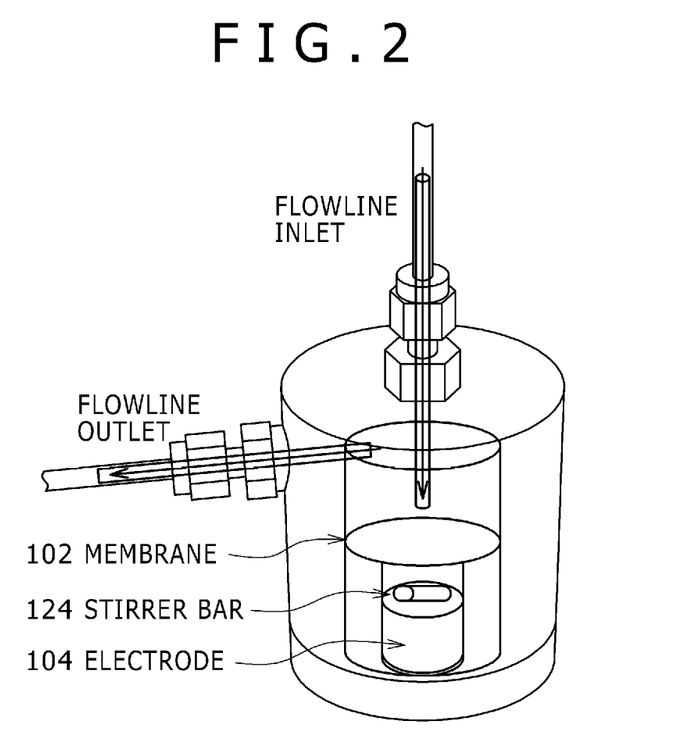
FIG. 2 displays a side view of a device according to some embodiments with a magnetic stirrer.

In some examples, as shown in FIG. 2, a magnetic stirrer (124) is placed inside the sensing chamber. The device can further comprise an external magnetic drive positioned outside the sensing chamber for activating the magnetic stirrer (124). Once activated, the magnetic stirrer (124) facilitates mixing of the mediating fluid (110). In some examples, the magnetic stirrer (124) can comprise a magnetic stir bar. The magnetic stir bar (124) can be placed between the electrode (104) and the membrane (102).

Figure 3A:
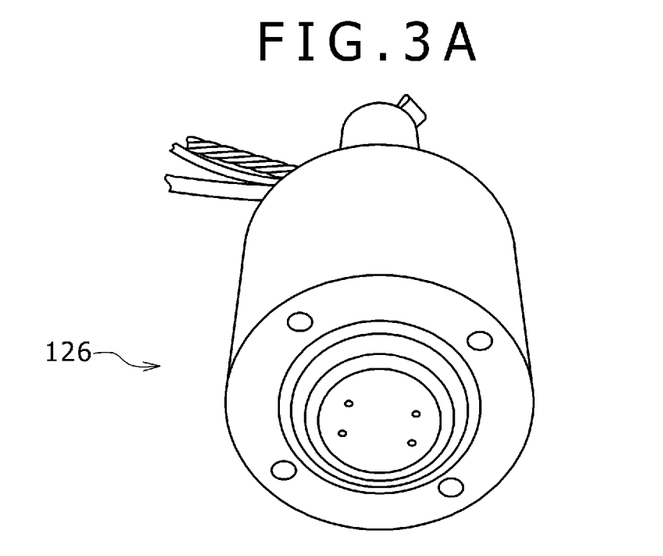
FIGS. 3A and 3B display a system according to some embodiments with a magnetic stir bar that sits in a pocket in the active measuring area.
Figure 3B:
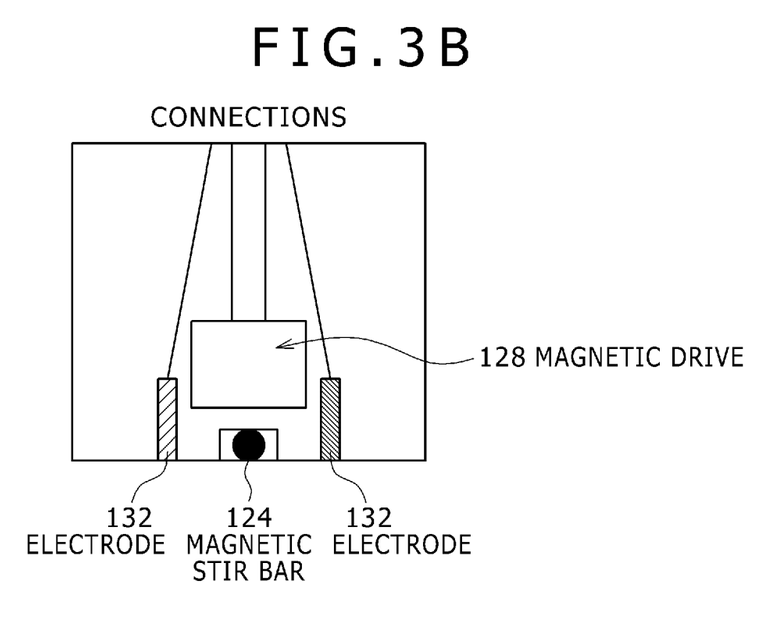
Figure 4:
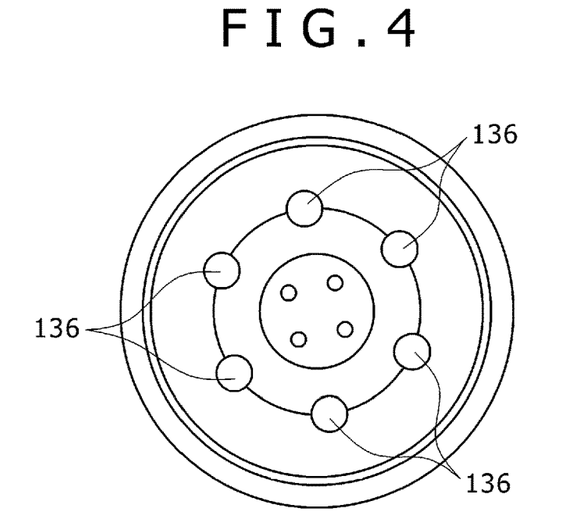
FIG. 4 displays an element according to some embodiments comprising a plurality of magnetic stirrer bars placed in pockets around the active measuring area.

In some examples, the external magnetic drive can comprise one or more magnets affixed to the housing, for example, at the bottom of the housing, for activating the magnetic stirrer in the sensing chamber. For example, FIGS. 3A and 3B illustrate a device (126) including a magnetic drive (128) provided in the center of the device, a magnetic stir bar (124), and two electrodes (130, 132). FIG. 4 includes six magnets (136) for activating corresponding magnetic stirrers (not shown). The magnets can be rare earth magnets. In some examples, an electromagnet is used as the external magnetic drive for activating the magnetic stirrer.

Figure 5:
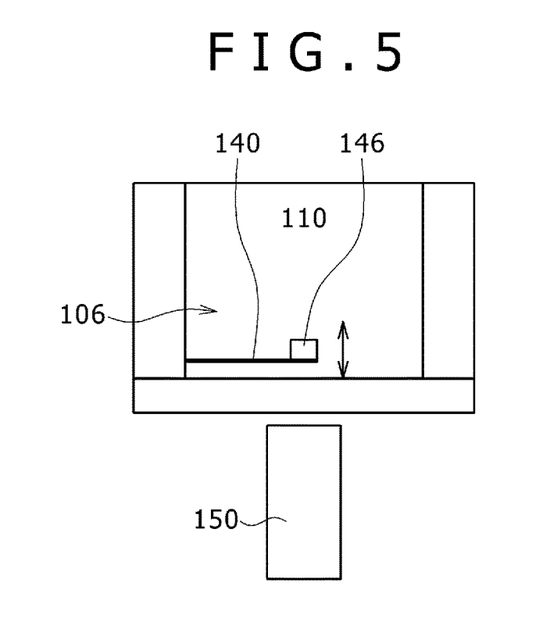
FIG. 5 displays a schematic drawing of a waggler type agitator according to some embodiments.

In some examples, referring now to FIG. 5, the device (100) comprises a magnetic element (146) tethered to a shim (140) (the magnetic element and shim also known as a "waggler") positioned in the mediating fluid (110) and an electromagnet (150) positioned outside the sensing chamber (106). The magnetic element (146) can be any element capable of magnetic attraction and/or repulsion in response to the induced magnetic force field from the electromagnet, such as a small steel circular disc. An induced electromagnetic force field from the electromagnet (150) acts upon the magnetic element (e.g., steel disc) (146) and the shim (140) vibrates from the attraction and/or repulsion of the magnetic element (146) to the electromagnet (150). By activating the waggler, a wave movement causes liquid displacement to effect mixing and measurement. The magnetic attraction and/or repulsion and the frequency of the pulses can be a fixed frequency or varied pulse rate, thus affecting liquid agitation by affecting both the strength and rapidity of the waggler.

Figure 6:
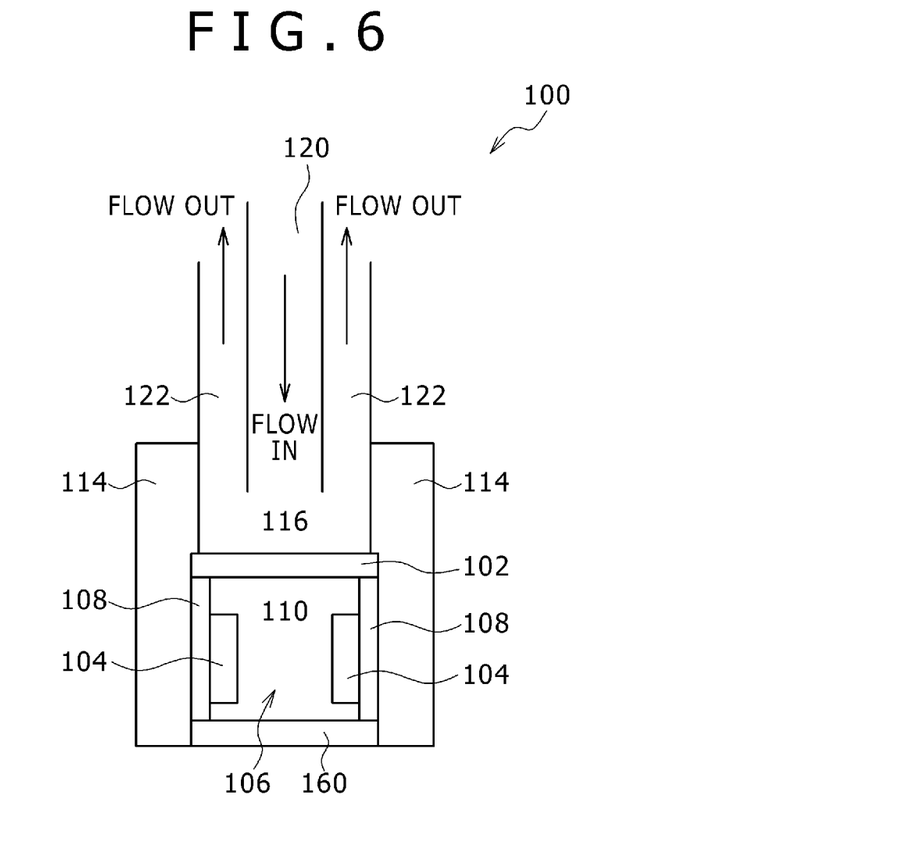
FIG. 6 displays a schematic drawing of a device according to some embodiments with a diaphragm.
Figure 7:
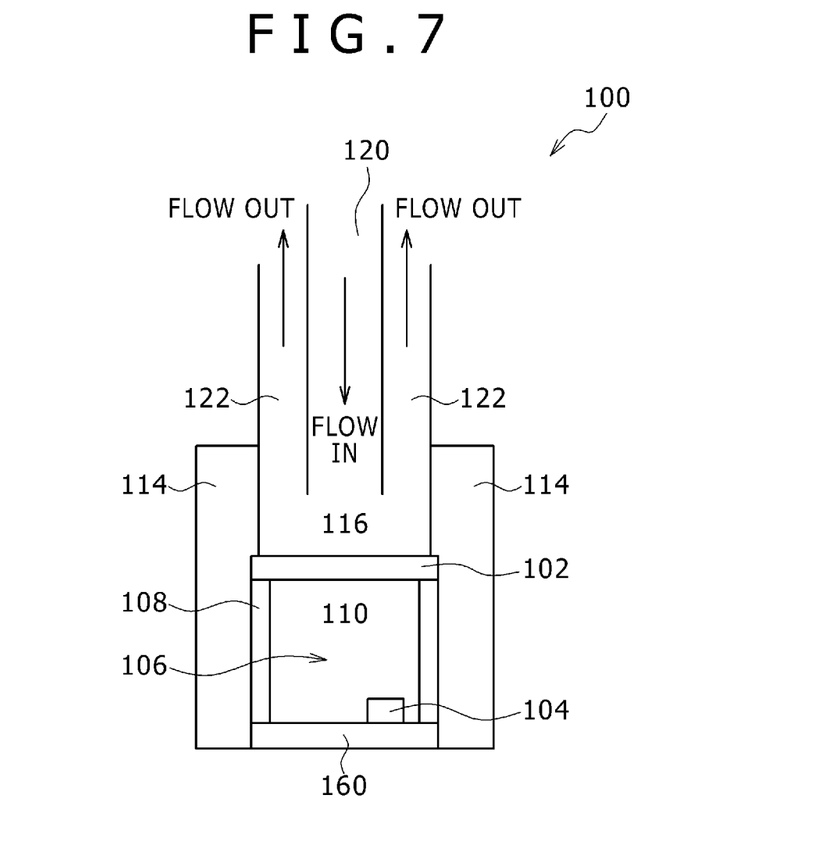
FIG. 7 displays a schematic drawing of a device according to some embodiments with a diaphragm.

In some examples, as shown in FIG. 6, the device (100) comprises a diaphragm (160), wherein the sensing chamber (106) can be defined by the membrane (102), the diaphragm (160), and the chamber wall (108). For example, the diaphragm (160) can be a 0.05 inch stainless steel machined circular disc that is clamped between Viton®/vitrile O-rings in the sensing chamber (106). The diaphragm (160) is capable of flexing/vibrating in an up and down motion to agitate the mediating fluid (110). As shown in FIG. 6, the electrode (104) can, for example, be affixed to the chamber wall (108). In some examples, as shown in FIG. 7, wherein the device (100) comprises a diaphragm (160), the electrode (104) can be affixed to the diaphragm (160).

Figure 8:
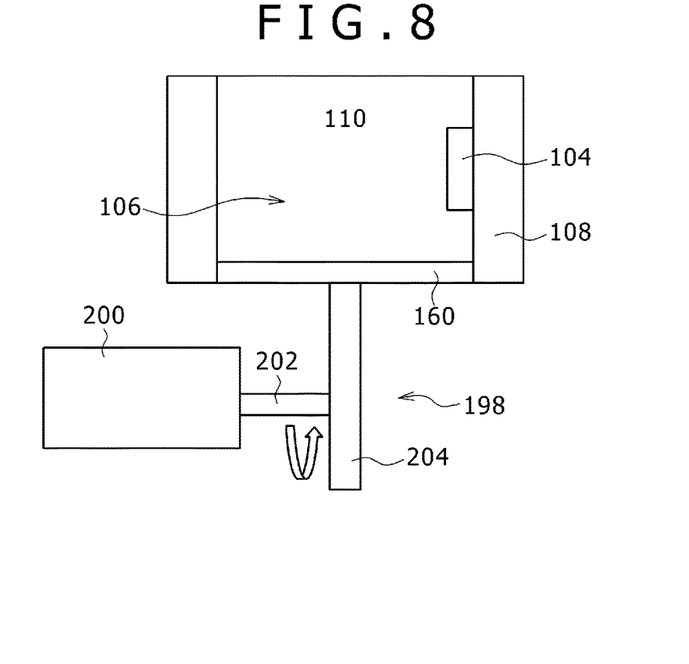
FIG. 8 displays a schematic drawing of a motor driven agitator according to some embodiments.

In some examples, as shown in FIG. 8, the diaphragm (160) is affixed to a motor driven agitator (198) such as an eight sprocket mechanical rotator positioned outside the sensing chamber (106) that is capable of agitating the mediating fluid (110) by flexing the diaphragm (160) in an up and down motion. The electrode (104) can be affixed, for example, to the chamber wall (108). The motor driven agitator (198) can comprise a motor (200) with a rotatable output shaft (202). A cogged wheel (204) can be affixed to the rotatable output shaft (202) of the motor (200). The cogged wheel (204) can be in physical contact with the diaphragm (160) such that when the motor (200) rotates the rotatable output shaft (202), the cogged wheel (204) rotates and flexes the diaphragm (160) to agitate the mediating fluid (110).

Figure 9:
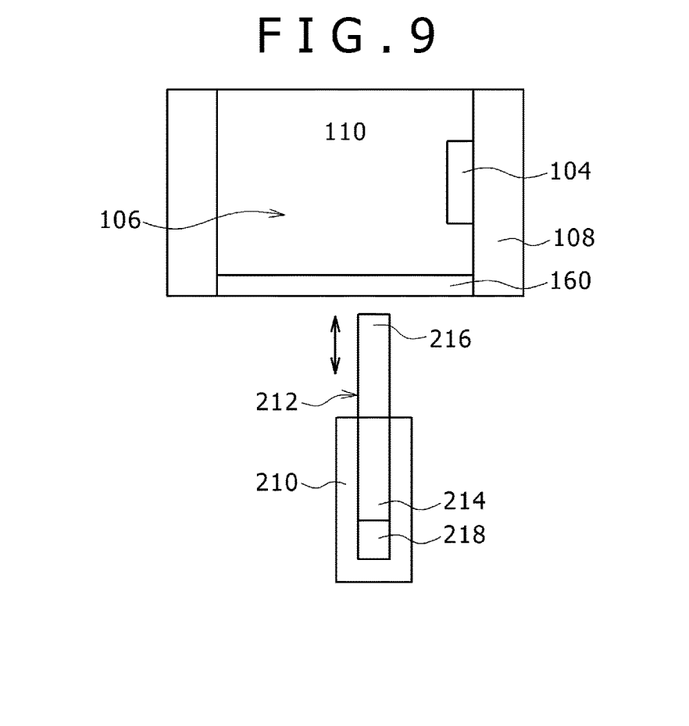
FIG. 9 displays a schematic drawing of a pulsed solenoid agitator according to some embodiments.

In some examples, as shown in FIG. 9, a pulsed solenoid agitator (210) is positioned outside the sensing chamber (106) that is capable of agitating the mediating fluid (110) by flexing the diaphragm (160). The electrode (104) can be affixed, for example, to the chamber wall (108). The solenoid (210) can comprise a wire wound field coil solenoid, inside of which is a free moving rod (212), comprising a first end (214) and a second end (216). The first end (214) of the rod (212), which can be positioned inside the solenoid field coil, can be in contact with a spring (218). The spring (218) can position the rod (212) such that, in the absence of an electric field, the second end of the rod (216) can be in contact with the diaphragm (160). When an appropriate electric current is applied to the solenoid (210), the rod (212) overcomes the counteracting force of the spring (218) to retract inside the solenoid body, such that the second end of the rod (216) is not in contact with the diaphragm (160). Thus, by pulsing the electric current the solenoid (210) can cause physical displacement of the rod (212) and can allow the rod (212) to flex the diaphragm (160). This oscillation of the rod (212) in an up/down action can flex/vibrate the diaphragm (160) thus agitating the mediating liquid. The intensity of the vibrations can be controlled by the amplitude of the electric field induced in the solenoid coil and the frequency of the electric pulses. Other methods of control also exist, including, for example, changing the design and type of the solenoid, the physical distance of the movement of the solenoid rod, the position of the solenoid in relationship to the diaphragm and the type and strength of the spring used and its physical position.

Figure 10:
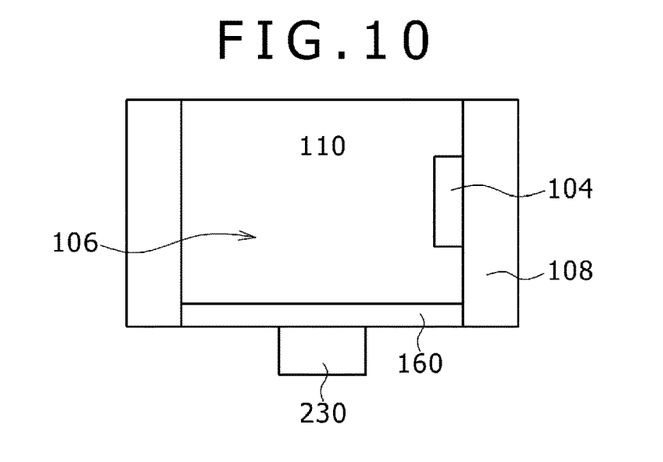
FIG. 10 displays a schematic drawing of a high frequency ultrasonic agitator according to some embodiments.

In some examples, as shown in FIG. 10, a high frequency ultrasonic agitator (230) positioned outside the sensing chamber (106) that is capable of agitating the mediator fluid by flexing the diaphragm (160). The electrode (104) can be affixed, for example, to the chamber wall (108). The high frequency ultrasonic agitator (230) can be affixed to the diaphragm (160) outside of the sensing chamber (106). The high frequency ultrasonic agitator (230) can comprise a piezoelectric generator disc that is affixed to the diaphragm (160). The power to the piezoelectric generator disc can be supplied by a small electronic fixed frequency power generator. The high frequency ultrasonic agitator (230) can turn high frequency electronic pulses into physical vibrations. The intensity of the vibrations from the high frequency ultrasonic agitator (230) can, for example, be controlled by the amplitude and frequency of the electronic pulses.

In some examples, an electroactive polymer can be used adjacent the mediating fluid (110). The electroactive polymer can, for example, be provided on or as at least a portion of the wall (108) of the sensing chamber. Alternatively, in embodiments as described herein where a shim or diaphragm is used, at least a portion of the shim or diaphragm can be formed of an electroactive polymer. Upon application of an appropriate electrode potential, the electroactive polymer can produce vibrations in the mediating fluid (110) to create agitation of the mediating fluid (110).

The electroactive polymer can be ionic or electronic. The electroactive polymers are driven by Coulomb forces and they include electrostrictive materials, electrostatic materials, piezoelectric materials, and ferroelectric materials. Ferroelectric materials can be made to hold the induced displacement while activated under a DC voltage, allowing them to be considered for robotic applications. Mostly, these materials have a greater mechanical energy density and they can be operated in air with no major constraints. Ionic electroactive polymers are materials that involve mobility or diffusion of ions. A system incorporating ionic electroactive polymers can comprise two electrodes and electrolyte. Such a system would offer advantages to a traditional three electrode sensor. The activation of the ionic electroactive polymer can be achieved by application of 1-2 V. The motions of the ionic electroactive polymers predominately involve bending displacement. Examples of ionic electroactive polymer materials include gels, oligomer metal composites, conductive polymers (CPs), and carbon nanotubes. The induced displacement of both the electronic and ionic EAPs can be designed geometrically to bend, stretch, or contract.

In some examples, a testing fluid can be provided in contact with the membrane for a time sufficient to allow the analyte when present to diffuse through the membrane into the mediating fluid of the sensing chamber. The testing fluid can comprise, for example, a well fluid, a biogas, water, or combinations thereof. In some examples, the analyte can comprise $H_2$, $O_2$, $CO_2$, $CH_4$, $C_2H_6$, or combinations thereof. In some examples, the analyte is $H_2S$. The analyte concentration can then be measured adjacent the active measuring area.

As noted above, the device can comprise an electrochemical device, wherein the active measuring area includes an electrode, and the analyte concentration can be determined through the use of the electrode. In some embodiments, the device can comprise an optical device and at least a portion of the device (e.g., the wall or bottom of the device) can be transparent to allow measurement of the analyte using, for example, a light transmitter and means for measuring the wavelength of light transmitted or reflected by the mediator fluid.

The device can be provided in any location where accurate measurement of an analyte is desired. For example, the device can be provided downhole in a well.

In a simple gas diffusion cell, there are three factors that can affect diffusion of the analyte toward the active measuring area in the sensing chamber: the first is the boundary layer on the top of the membrane, the second is the membrane itself, and the third is diffusion in the sensing chamber. It is desirable in the devices herein to minimize the effect of the three factors. The outer boundary layer is governed by the flow rate in the outside flow and in the case of downhole sensors this is not rate limiting. The membrane response is governed by the permeability of the membrane (the time for the gaseous analyte to pass through it) which is determined by the properties of the membrane. The sensing chamber response is dependent on the cell volume, which, when the active measuring area is provided at the base of the cell, depends on the cell depth. In these situations, the type of detection method used (optical, electrochemical, etc.) will have no effect on the response time as the time to reach equilibrium within the sensing chamber will dominate. Accordingly, the devices and methods provided herein enhance the time to reach equilibrium by minimizing the time for the gas to diffuse throughout the chamber, so that analyte measurement moves away from systems in which diffusion dominates to a system where convection dominates.

By way of non-limiting illustration, examples of certain embodiments of the present disclosure are given below.

EXAMPLES

Example 1

Example 1 is based on an electrochemical gas sensor for the determination of $H_2S$ as shown schematically, for example, in FIGS. 1 and 2. The sensor includes a membrane to separate the measurement cell (sensing chamber) containing an electrolyte, from the wellbore fluids within a sampling flow line. In this example, the flow was directed onto the front of the membrane unit to ensure that the boundary layer caused by the flow of the sample solution across the membrane was not the rate determining step for the response time. Below the sample flow, the membrane was provided and the electrode was provided a set distance from the membrane.

Preliminary results focused on examining the response time of the sensor when the electrode was provided approximately 0.5 mm from the back support of the membrane unit under static conditions. The flowline was filled with water initially. The flow rate of the flowline was set at 200 mL/min and data was recorded periodically (ca. 5 mins) whilst the sample solution was flowing. After a set period of time, the water in the flowline was replaced with a solution containing a known concentration of the analyte. The peak current was then recorded as a function of time.

Figure 11:
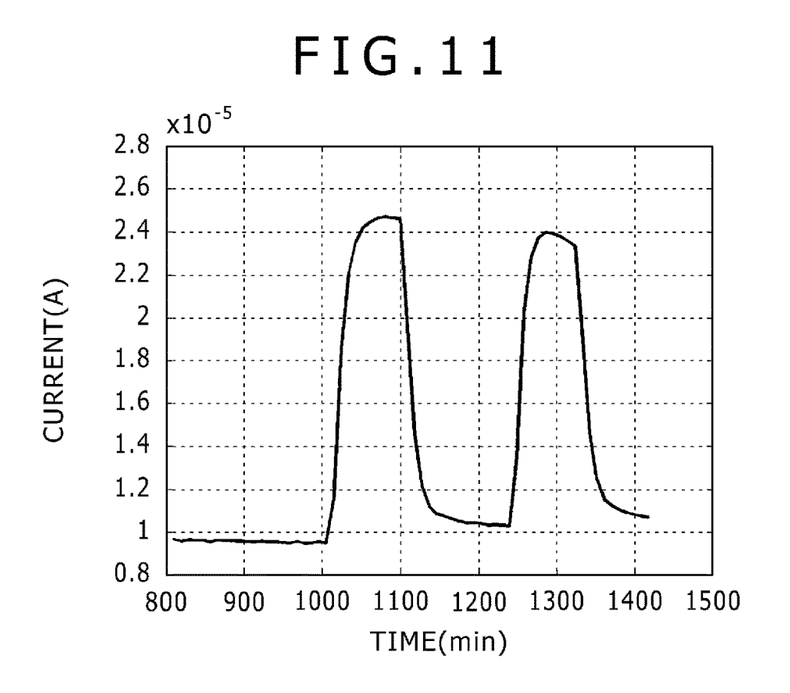
FIG. 11 displays the variation in oxidative peak current measured according to a comparative example with a cell depth of 0.5 mm, wherein a 1.1 mM hydrogen sulfide solution (aqueous) is introduced and removed from the flow line.

FIG. 11 displays a plot of the oxidative peak current as a function of time for a series of these types of experiments. In an initial experiment, no element was used to produce convection in the sensing chamber. From 0 to 1000 minutes, the signal was very stable as illustrated between 800 and 1000 minutes in FIG. 11. This indicates that there was no leakage from inside the cell into the flowline (which would have been indicated by a decreasing peak current) and therefore the membrane had achieved good sealing. At 1000 mins, an aqueous hydrogen sulfide solution (1100 μM) was injected into the flowline solution and a rise in the oxidative peak current was observed, consistent with the electrocatalytic reaction occurring, which then reached a plateau once the cell reached equilibrium. At 1100 minutes, the hydrogen sulfide solution was removed from the flowline and replaced with a fresh water solution and a decrease in the current was recorded. This experiment was then repeated at 1250 mins with an analogous result observed. The cell response time, meaning the time taken for 90% of the signal to be achieved, was found to be 40 to 50 mins.

Example 2

Figure 12:
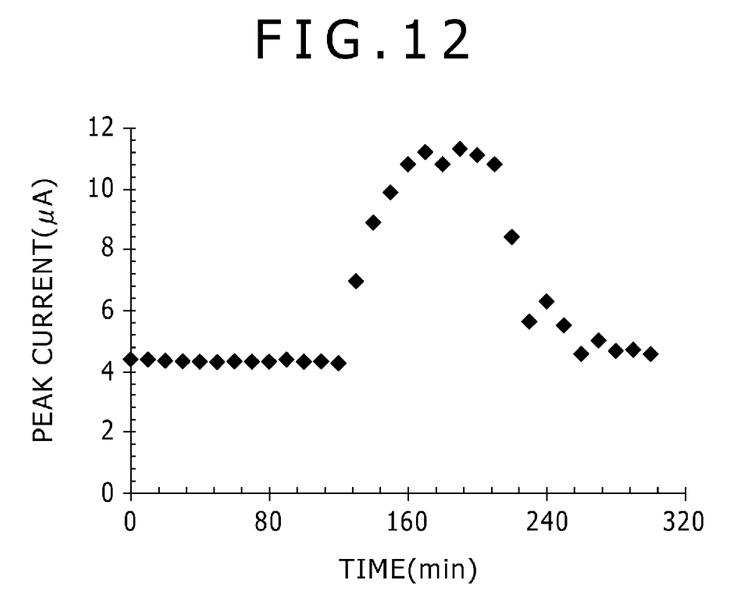
FIG. 12 displays the variation in oxidative peak current measured in the cell according to some embodiments at a cell depth of 1.8 mm, wherein a 0.5 mM hydrogen sulfide solution is introduced and removed from the flowline.

In Example 2, a small magnetic stirrer was placed between the electrode and the membrane unit and the stirrer was driven by an external magnetic drive, placed outside the cell. In order to incorporate the stirrer the cell depth was initially increased from 0.5 mm to 1.8 mm. It should be noted that in this case the cell was agitated between each cyclic voltammetric measurement; however, 20 seconds prior to and during the scan the cell was held under quiescent conditions. Once again the response was recorded before, during, and after a hydrogen sulfide solution was added to the flowline; however, a 0.5 mM hydrogen sulfide solution was introduced into the flowline in this example. The corresponding plot of peak current as a function of time is illustrated in FIG. 12. As expected, there was a rise and fall in the oxidative peak current as the hydrogen sulfide solution was first added and then subsequently removed from the flowline. Analysis of the plot in FIG. 12 shows that the response time of the sensor was found to be 40 to 50 mins, even though the cell depth was approximately 4 times deeper than the cell depth of the static cell shown in FIG. 11. These results suggest that the response time can be improved further by decreasing the cell depth.

Example 3

Figure 13A:
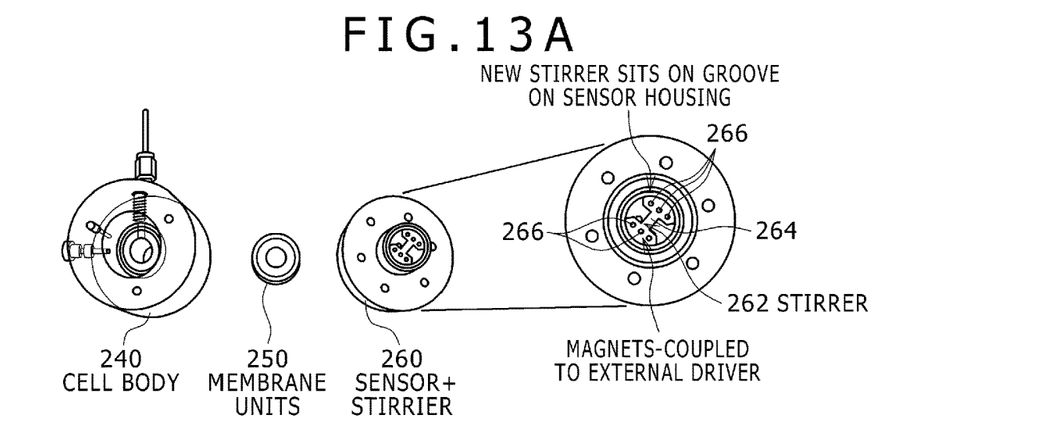
FIGS. 13A, 13B and 13C display a system according to some embodiments comprising a magnetic stirrer.
Figure 13B:
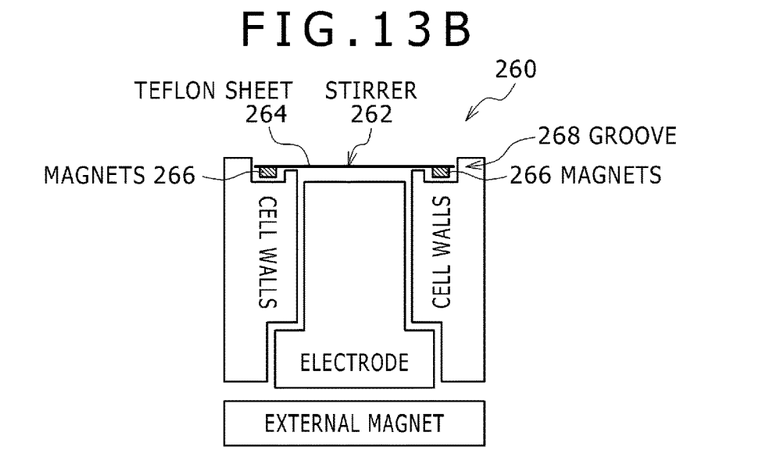
Figure 13C:
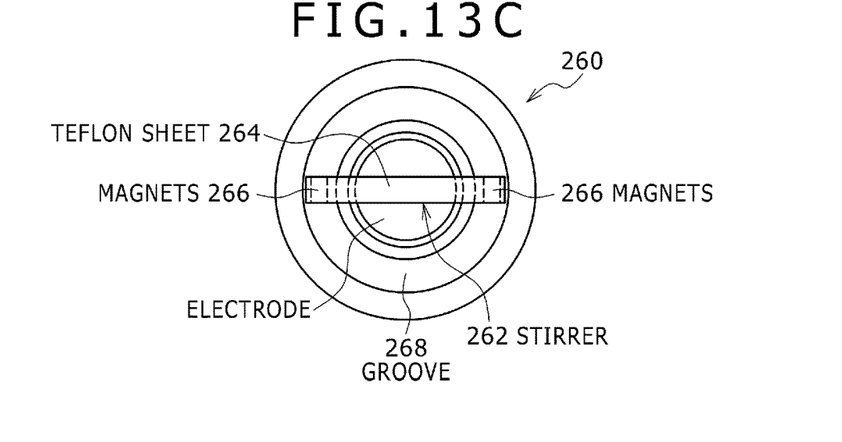

To decrease the cell depth further, and hence lower the response time of the sensor, an alternative magnetic stirrer system was produced. FIG. 13A illustrates the alternative stirrer design comprising a cell body (240), a membrane unit (250), and a sensor housing (260). A schematic side view of the sensor housing (260) is illustrated in FIG. 13B, wherein a stirrer (262) comprises rare-earth magnets (266) within a thin shaped Teflon sheet (264) and the stirrer (262) is provided in a groove (268) in the sensor housing (260). A schematic top view of the sensor housing is shown in FIG. 13C. Using this system it was found that cell depths between 1.1 and 0.7 mm were achievable.

Figure 14:
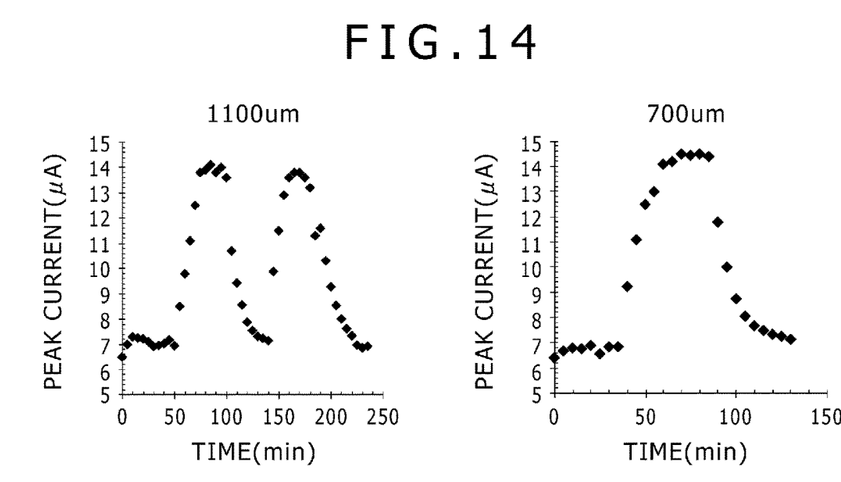
FIG. 14 displays the variation in oxidative peak current measured in the cell at cell depths of 1.1 and 0.7 mm as a 0.5 mM hydrogen sulfide solution is introduced and removed from the flowline.

FIG. 14 details the response using this alternative system for the cell depths of 1.1 and 0.7 mm, respectively, when a 0.5 mM hydrogen sulfide solution was introduced and removed from the flowline. In this case, a response time of 25 to 30 mins was achieved for the 1.1 mm cell depth and 25 mins for the 0.7 mm cell depth.

Example 4

Figure 15:
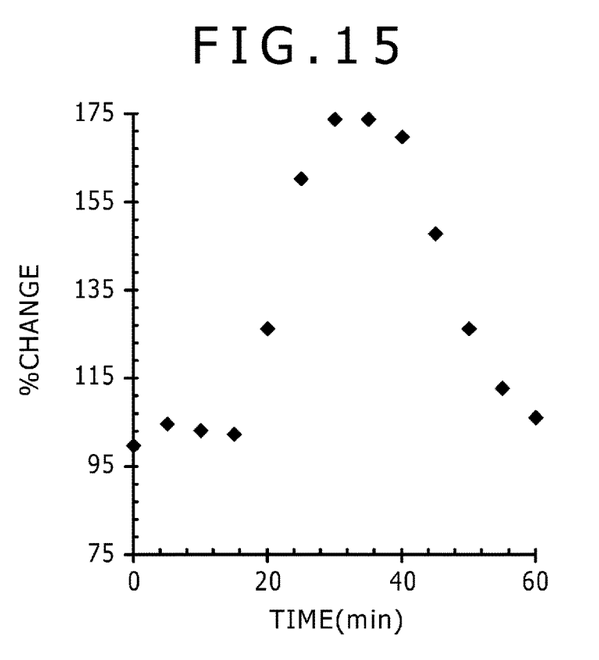
FIG. 15 displays the variation in oxidative peak current measured when using a 6 magnet collar for a magnetic stirrer as a 0.6 mM hydrogen sulfide solution is introduced and removed.

An alternative system was tested whereby the magnetic stirrers were placed in pockets around the electrodes, as shown in FIG. 4, with a cell depth of 0.5 mm. In this case, the 0.6 mM hydrogen sulfide solution was introduced at 20 minutes and a response time of 15-20 minutes was observed as shown in FIG. 15. Although the magnet pockets served as dead spaces for the H$_2$S so the time to degas was evidently slower, this prototype performed better than the prototype in Example 3, wherein the stirrer did not appear to work as efficiently.

Example 5

Figure 16:
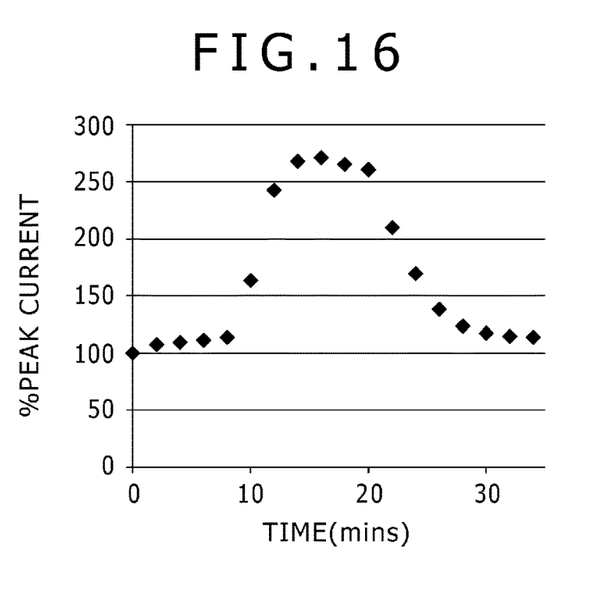
FIG. 16 displays the variation in oxidative peak current measured in using a single magnet prototype as 1.2 mM hydrogen sulfide solution is introduced and removed.

Another prototype was constructed that consists of a single magnet that sits in a pocket in the middle the electrode, as shown in FIG. 3, with a cell depth of 0.5 mm. In this case, the 1.2 mM hydrogen sulfide solution was introduced at 10 minutes and a response time of 8-10 minutes was observed as shown in FIG. 16.

Examples 6-9

Along with the magnetic stirring approaches detailed above, other concepts were tested wherein convection of the mediating fluid was produced. In Example 6, a motor driven agitator as shown in FIG. 8, was used. The motor driven agitator was a small geared down electric DC motor rotating continually at 40 RPM. The rotating motor output shaft projected into a space below an upper sealed and divided circular chamber including the mediating fluid. On this motor shaft was affixed a machined circular disc of an eight sprocket mechanical rotator which was in physical contact with the underside of a 0.05 mm thick circular disc clamped between Viton/vitrile O rings within the top and bottom halves of two separate chambers divided by O ring seals around the circumference of the 0.05 mm circular diaphragm. The machined eight point rotating sprocket vibrated and physically displaced the thin diaphragm, which transferred energy in an up down movement to agitate the liquid medium into a gentle mixing motion of approximately 320 movements per minute.

Example 7 tested the use of a waggler agitator as shown in FIG. 5.

In Example 8, a pulsed solenoid agitator was tested as shown in FIG. 9 using a 0.05 inch stainless steel diaphragm.

In Example 9, a high frequency ultrasonic agitator was tested as shown in FIG. 10 using a 0.05 inch stainless steel diaphragm.

Figure 17:
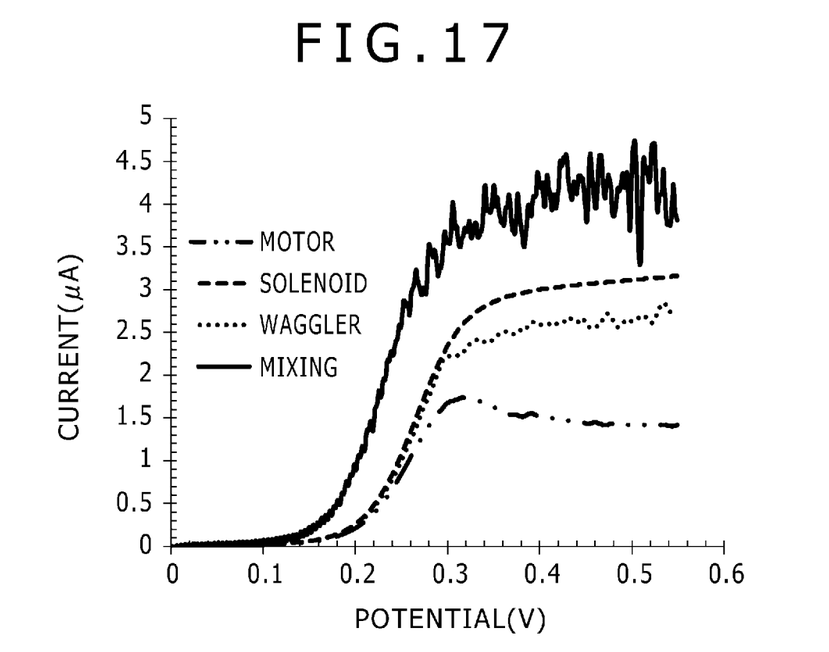
FIG. 17 displays the steady state linear sweep voltammetry for multiple devices disclosed herein.

FIG. 17 displays the corresponding linear sweep voltammetry results for each of the methods in Examples 2 and 6-8, wherein the electrode was placed in a solution containing 0.5 mM t-butylferrocene sulfonate, and the height of the steady state limiting current provides a qualitative estimate of the efficiency of the mixing. As shown in FIG. 17, the vibrating solenoid corresponding to Example 8 and labeled "Solenoid" produced the best mixing. The labels "Mixing", "Motor" and "Waggler" correspond to Examples 2, 6 and 7, respectively.

As used in the specification, and in the appended claims, the singular forms "a," "an," "the," include plural referents unless the context clearly dictates otherwise.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A device for sensing an analyte, the device comprising:
    a membrane that allows diffusion of an analyte;
    an active measuring area for measuring a concentration of the analyte;
    a sensing chamber situated between the membrane and the active measuring area, the sensing chamber including a wall and comprising a mediating fluid, the sensing chamber being defined by the membrane, the active measuring area and the wall; and
    an element for producing convection within the mediating fluid to facilitate mixing of the analyte diffusing through the membrane in the mediating fluid to thereby reduce a response time for the active measuring area to measure the presence of the analyte in the mediating fluid.

2. The device of claim 1, wherein the element comprises a magnetic stirrer placed inside the sensing chamber.

3. The device of claim 2, wherein the device further comprises an external magnetic drive positioned outside the sensing chamber for activating the magnetic stirrer.

4. The device of claim 1, wherein the device further comprises a diaphragm adjacent the sensing chamber and the element is capable of vibrating the diaphragm to agitate the mediating fluid.

5. The device of claim 4, wherein the element comprises a motor driven agitator positioned outside the sensing chamber that is capable of agitating the mediating fluid through the diaphragm.

6. The device of claim 4, wherein the element comprises a pulsed solenoid agitator positioned outside the sensing chamber that is capable of agitating the mediating fluid through the diaphragm.

7. The device of claim 4, wherein the element comprises a high frequency ultrasonic agitator positioned outside the sensing chamber that is capable of agitating the mediating fluid through the diaphragm.

8. The device of claim 1, wherein the element comprises a high frequency ultrasonic agitator positioned inside the sensing chamber that is capable of agitating the mediating fluid.

9. The device of claim 1, wherein the element comprises a magnet tethered to a shim positioned in the mediating fluid and an electromagnet positioned outside the sensing chamber, wherein the shim is capable of vibrating when subjected to a magnetic field from the electromagnet.

10. The device of claim 1, wherein the device comprises an electrochemical device.

11. The device of claim 10, wherein the active measuring area includes an electrode.

12. The device of claim 1, wherein the analyte is selected from the group consisting of $H_2$, $O_2$, $CO_2$, $CH_4$, and $C_2H_6$.

13. The device of claim 1, wherein the analyte is $H_2S$.

14. The device of claim 1, further comprising a first channel for directing the flow of a testing fluid towards the membrane and a second channel for directing the flow of the testing fluid away from the membrane.

15. A method of measuring an analyte concentration of a testing fluid, the method comprising:
    providing a device, comprising:
        a membrane that allows diffusion of an analyte,
        an active measuring area for measuring a concentration of the analyte,
        a sensing chamber situated between the membrane and the active measuring area, the sensing chamber including a wall and comprising a mediating fluid, the sensing chamber being defined by the membrane, the active measuring area and the wall, and
        an element for producing convection within the mediating fluid;
    contacting the testing fluid with the membrane for a time sufficient to allow the analyte when present to diffuse through the membrane into the mediating fluid of the sensing chamber;
    producing convection in the sensing chamber using the element to facilitate mixing of the mediating fluid; and
    measuring the analyte concentration adjacent the active measuring area.

16. The method of claim 15, wherein the element comprises a magnetic stirrer placed inside the sensing chamber and the method further comprises applying a magnetic field to the magnetic stirrer to produce convection in the sensing chamber.

17. The method of claim 15, wherein the device further comprises a diaphragm adjacent the sensing chamber and the method further comprises vibrating the diaphragm to agitate the mediating fluid.

18. The method of claim 15, wherein the element comprises a high frequency ultrasonic agitator positioned inside the sensing chamber and the method comprises agitating the mediating fluid.

19. The method of claim 15, wherein the element comprises an electroactive polymer adjacent the mediating fluid and the method comprises applying a potential to the electroactive polymer to cause the electroactive polymer to expand and contract and produce convention in the mediating fluid.

20. The method of claim 15, further comprising directing the flow of the testing fluid towards the membrane using a first channel to allow contact of the testing fluid with the membrane and then directing the flow of the testing fluid away from the membrane using a second channel.

* * * * *